United States Patent [19]

Bernhardt et al.

[11] Patent Number: 4,675,422

[45] Date of Patent: Jun. 23, 1987

[54] ORGANOMETALLIC COMPOUNDS

[75] Inventors: Randal J. Bernhardt, Mundelein; Melvin L. Loeb, Northbrook, both of Ill.; James W. Kay, Durham Township, Pa.

[73] Assignee: Stepan Company, Northfield, Ill.

[21] Appl. No.: 790,486

[22] Filed: Oct. 23, 1985

[51] Int. Cl.$^4$ .............................................. C07F 5/06
[52] U.S. Cl. ...................................... 556/13; 556/24; 556/183; 260/404; 260/414
[58] Field of Search ............... 260/414, 404; 556/13, 556/24, 183

[56] References Cited

U.S. PATENT DOCUMENTS

| | | | |
|---|---|---|---|
| 2,101,323 | 12/1937 | Salzberg | 260/108 |
| 2,604,449 | 7/1952 | Bryant et al. | 556/183 X |
| 2,768,138 | 10/1956 | Hotten et al. | 252/35 |
| 2,849,401 | 8/1958 | Hotten | 556/183 X |
| 3,164,557 | 1/1965 | Merten et al. | 260/2.5 |
| 3,365,477 | 1/1968 | Gee et al. | 556/183 X |
| 3,377,197 | 4/1968 | Erby et al. | 556/183 X |
| 3,514,400 | 5/1970 | Hotten | 252/18 |
| 3,591,505 | 7/1971 | Polishuk | 252/37.7 |
| 3,644,513 | 2/1972 | Sweeney et al. | 556/183 X |
| 3,776,846 | 12/1973 | Bailey et al. | 252/37.7 |
| 3,791,972 | 2/1974 | Myers | 252/37.7 |
| 3,836,551 | 9/1974 | Schroeder et al. | 556/183 X |
| 3,905,936 | 9/1975 | Hawthorne | 260/40 R |
| 3,966,902 | 6/1976 | Chromecek | 424/59 |
| 4,013,699 | 3/1977 | Passedouet et al. | 556/183 X |
| 4,089,954 | 5/1978 | Morelle et al. | 556/183 X |
| 4,090,886 | 5/1978 | Turner | 106/264 |
| 4,098,758 | 7/1978 | Monte et al. | 260/42.14 |
| 4,122,062 | 10/1978 | Monte et al. | 260/42.14 |
| 4,280,917 | 7/1981 | Pratt | 252/37.7 |
| 4,324,670 | 4/1982 | Pratt | 252/37.7 |
| 4,360,670 | 11/1982 | Bechara et al. | 544/64 |
| 4,478,959 | 10/1984 | Bechara | 521/124 |

FOREIGN PATENT DOCUMENTS

| | | |
|---|---|---|
| 1124424 | 5/1982 | Canada . |
| 0018780 | 11/1980 | European Pat. Off. . |
| 1453956 | 10/1976 | United Kingdom . |
| 1544405 | 4/1979 | United Kingdom . |
| 1556376 | 11/1979 | United Kingdom . |

*Primary Examiner*—Helen M. S. Sneed

[57] ABSTRACT

Organometallic compounds and compositions comprising a metal, an amido carboxyl moiety bonded to the metal, an active moiety bonded to the metal, and at least one modifier moiety sufficient to satisfy the valency of the metal. These compounds and compositions are capable of combining the substantivity of the amido carboxyl metal system, functional efficacy of an active moiety, and film-forming properties in a single compound or composition.

2 Claims, No Drawings

ORGANOMETALLIC COMPOUNDS

FIELD OF THE INVENTION

This invention relates to organometallic compounds, to compositions of such compounds and to formulations incorporating such compounds and compositions.

BACKGROUND OF THE INVENTION

Complex organometallic soaps are known in the art. Metallic soaps have long been used in a variety of applications, including such uses as gelling agents for hydrocarbons, as drying agents for paints and varnishes, as catalysts, as surface active agents and the like. More specifically, organometallic compounds of aluminum, titanium, tin and zirconium are known.

Complex aluminum soaps comprising variously substituted carboxylic acid anions have long been used as gelling agents in grease compositions. Illustrative patents disclosing such soaps for grease applications are U.S. Pat. Nos. 2,768,138, 3,591,505, and 4,280,917.

Organoaluminum compounds have also been used in air drying compositions such as paints and varnishes and the like. For example, U.S. Pat. No. 4,090,886 discloses an air drying media which contains an organoaluminum compound. The media is stated to be stable for storage, although it includes an aluminum compound at a ratio of aluminum complex to reactive paint media which would otherwise be unstable and which would be expected to gel prior to application. The organoaluminum compound disclosed in U.S. Pat. No. 4,090,886 comprises certain labile monofunctional reactants which it is stated will react preferentially to impede the complex association which would otherwise occur when aluminum compounds are added to drying oils or paint media which contain reactive groups, such as, for example, hydroxyl and carboxyl radicals. The organoaluminum compounds disclosed in U.S. Pat. No. 4,090,886 may include moieties from monocarboxylic acids, half-esters of dicarboxylic acids and aminocarboxylic acids.

Organotin compounds, and more particularly tin carboxylates, are well known as catalysts for the reaction between an organic isocyanate and organic compounds having an active hydrogen group in the preparation of polyurethane. For example, U.S. Pat. No. 4,360,670 discloses amino and amido dialkyl tin dicarboxylates useful as high activity polyurethane catalysts.

Organotitanium compounds are also known. Such compounds may be prepared from tetraalkyl ortho titanates by reaction with organic acids. Thus, organo-titanates comprising carboxylates are disclosed in U.S. Pat No. 4,098,758 and alkoxy titanate salts useful as surface active agents are disclosed in U.S. Pat. No. 4,122,062.

U.S. Pat. No. 4,098,758 discloses an organo-titanate having non-hydrolyzable carboxylate groups preferably formed from organic acids having 6 to 24 carbon atoms. It is stated that the carboxylate group may be substituted with amino and carboxyl groups as well as other substituents and may contain intermediate hetero atoms, including nitrogen, among others.

In U.S. Pat. No. 4,122,062 the alkoxy titanate salts disclosed include one moiety selected from the group consisting of thioaroxy, sulfonyl, sulfinyl, diester pyrophosphate, diester phosphate or substituted derivatives thereof, and another moiety which is an acyloxy or aryloxy.

Polymer complex carriers for an active ingredient are disclosed in U.S. Pat. No. 3,966,902. The polymer comprises a monomer having hydrophilic functional groups and contains aluminum, zinc, or zirconium bound in complex form.

Despite the broad and varied scope of the organometallic art, no disclosure is made of organometallic compounds which are substantive, and which can be modified with an active moiety to adapt the resulting compound to a particular end use of choice. In addition, none of the art is directed to an organometallic compound which combines in a single compound both an amido carboxyl moiety and an active moiety.

Accordingly, it is a primary object of the present invention to provide an organometallic compound which is substantive to various types of surfaces, and which contains an active moiety which may be selected from a wide variety of organic compounds, depending upon the particular desired end use application of the organometallic compound. It is a related object to provide an organometallic compound which is substantive, includes an active moiety and is film-forming.

Another object of the present invention is to provide a substantive organometallic compound in which the relative degree of substantivity can be varied.

A further object of this invention lies in the provision of organometallic compounds which form films and which are substantive to a wide variety of substrates.

Yet another object of this invention is to provide organometallic compounds which are hydrophobic and in which the relative degree of hydrophobicity can be varied.

It is a further object of the present invention to provide an organometallic composition which is substantive to various types of surfaces, and which contains an active moiety which may be selected from a wide variety of organic compounds, depending upon the particular desired end use application of the organometallic composition. A related object is to provide an organometallic composition which is substantive, includes an active moiety and is film-forming.

Another object of this invention is to provide substantive organometallic compositions in which the relative degree of substantivity can be varied. A further object is to provide organometallic compositions which form films which are substantive to a wide variety of substrates.

Another object of the present invention is to provide organometallic compositions which are hydrophobic and in which the relative degree of hydrophobicity can be varied.

Yet another object of this invention is to provide formulations which include the substantive, active moiety-containing organometallic compounds and/or organometallic compositions described herein.

These and other objects and advantages of the present invention will be apparent from the following description of the invention.

SUMMARY OF THE INVENTION

The present invention is predicated on the discovery that an organometallic compound can be formed which includes both an amido carboxyl moiety and an active moiety selected from a wide variety of organic radicals capable of adapting the resulting compound to a particular end use of choice. The organometallic compounds of the present invention are characterized by their substantivity and by their variable degrees of hydrophobicity. Desirably the organometallic compounds of this invention will form a film when applied to a substrate.

As used herein, the term film-forming means that the organometallic compound, having been applied to a substrate, comprises a residual solid material which is not chalky, and will not flake, granulate or form a powder, as typically occurs with organic compounds, such as, for example, benzoic acid or the like, applied from an isopropyl alcohol solution.

The organometallic compounds of this invention form films which themselves may or may not be continuous, but which have the appearance of being continuous and will not fracture at random. The film so formed typically remains intact, even if the substrate to which it is adhered is removed. The film thus appears to be polymeric in nature although the actual structure is not currently known.

While the organometallic compounds of this invention are soluble or suspendable in the organic medium in which they are synthesized, when applied to a substrate and the solvent is removed, they form a solid, often a film, which will not readily redissolve or resuspend in like organic medium. The solid, or film, however, may decompose in a strong alkali solution.

The organometallic compounds of the present invention also display substantivity to the surface to which they are applied. Substantivity, as used herein, means that the compound, when applied to a substrate, will adhere to the surface and is not readily removed by common solvents such as water, acetone, alcohol and the like, nor can the compounds be easily removed by mechanical action such as rubbing. The compounds of the present invention may be substantive to polar surfaces, non-polar surfaces, or both, including, by way of illustration, and not in limitation, human skin, fabric, wood, paper, teflon, steel, glass and the like.

The organometallic compounds of the present invention comprise a trivalent or tetravalent metal, an amido carboxyl moiety bonded to the metal, an active moiety bonded to the metal and at least one modifier moiety bonded to the metal, the number of such modifier moieties being sufficient to satisfy the valency of the metal. The organometallic compounds of the present invention are thus capable of combining the substantivity of the amido carboxyl metal system, functional efficacy of an active moiety, and film-forming properties in a single compound.

The organometallic compounds of the present invention are useful in a wide variety of applications. These compounds may find utility in any field or application where a degree of substantivity and/or hydrophobicity, combined with chemical, biological or physical properties of specific active moieties, are desired. Moreover, the organometallic compounds of the present invention can be tailored to any particular end use application by appropriate selection of the active moiety, the metal, the amido carboxyl moiety and the modifier moiety.

While the description herein is directed to the organometallic compounds of the present invention, it should be understood that the description is likewise applicable to the organometallic compositions described in detail hereinafter.

DETAILED DESCRIPTION OF THE INVENTION

The organometallic compounds of the present invention are described by the general formula:

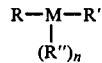

wherein M is a trivalent or tetravalent metal, R is an amido carboxyl moiety, R' is an active moiety, which may also be an amido carboxyl moiety, and R" is a modifier moiety capable of satisfying the valency of the metal, M. Depending upon the valency of the metal, n is either 1 or 2. More particularly, where the metal is trivalent, n is 1 and where the metal is tetravalent, n is 2.

Each moiety, R, R', R" and the metal M can affect the substantivity, film-forming character, hydrophobicity and functional activity of the organometallic compounds of this invention. None of the properties of these compounds is solely dependent on any one moiety, although each moiety does not necessarily affect each property to the same degree. Accordingly, it is the interdependency of each of these moieties, R, R', R" and M, which must be taken into account to provide a compound which not only has the desired activity for the end use application contemplated, but which will also have the film-forming characteristic, substantivity and hydrophobicity required to make the compound effective for that application.

Turning to the metal and moieties which comprise the organometallic compounds of the present invention, the metal M may be a metal which has a valency of at least three, trivalent and tetravalent metals being preferred. Suitable trivalent metals include aluminum and iron and suitable tetravalent metals include tin, titanium, and zirconium. Aluminum, titanium, tin, and zirconium are preferred. Aluminum is particularly preferred, because of its economy and non-toxicity.

The amido carboxyl moiety, R, may be saturated or unsaturated, aliphatic or aromatic. The preferred amido carboxyl moieties are those having either of the general formulas (a) or (b), whatever the derivation:

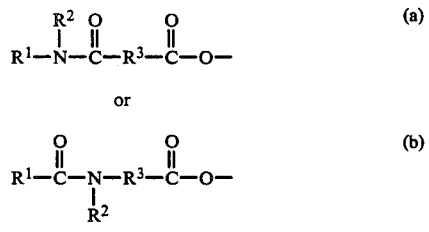

In the amido carboxyl moieties described by formulas (a) and (b), the radicals $R^1$ and $R^2$ may be the same or different, and are selected from the group consisting of hydrogen, an alkyl radical of from 1 to about 20 carbon atoms, an aryl, aralkyl, substituted aryl or substituted aralkyl radical of from 6 to about 20 carbon atoms or an alkenyl radical of from 3 to about 20 carbon atoms. The radicals $R^1$ and $R^2$ may be straight chain, branched, or substituted with halogen, hydroxyl and the like. The radical, $R^3$, in formulas (a) and (b) is a hydrocarbyl radical. The term hydrocarbyl radical as used herein means any carbon and hydrogen containing radical, including aryl, aralkyl substituted aryl and aralkyl radicals of from 6 to about 20 carbon atoms, alkyl and substituted alkyl radicals of from 1 to about 20 carbon atoms, and alkenyl and substituted alkenyl radicals of from 1 to about 20 carbon atoms. The radical, $R^3$, preferably comprises a hydrocarbyl radical of from 1 to about 6 carbon atoms. The hydrocarbyl radical, $R^3$, may be completely substituted with atoms such as halogen, as in, for example, the tetrabromophenylene radical.

It is believed that the amido carboxyl-metal system contributes to the film-forming characteristic, substantivity and hydrophobicity of the organometallic compounds of this invention. More particularly, it has been found that each of the carbon chain lengths of the radicals, $R^1$, $R^2$ and $R^3$, individually and collectively, may affect the properties of the final compound. Although the interrelationship of $R^1$, $R^2$ and $R^3$ is not at present fully understood, it has been found that the chain length of each of $R^1$, $R^2$ and $R^3$, and the total number of carbon atoms provided by these radicals must be taken into account in order to provide a compound with the desired properties.

For example, with respect to the hydrophobicity of the organometallic compounds, it has been found, generally, that if $R^1$ and $R^2$ are short, that is, the sum of the number of carbon atoms in $R^1$ and $R^2$ is less than about 4, then the compound is less hydrophobic than with longer chain lengths of $R^1$ and $R^2$, although substantivity appears to be satisfactory. On the other hand, as the chain length of each of $R^1$ and $R^2$, as well as the total number of carbon atoms of R increases, the hydrophobicity of the organometallic compound increases, and the solubility in isopropyl alcohol of the compound likewise increases. Substantivity, however, may decrease. Solubility of the compound tends to decrease as the overall carbon chain length of R exceeds about 12 to 15 carbon atoms or so. This may, for some compounds, affect film-forming and hydrophobicity depending on the active moiety, R', and modifier moiety, R".

Organometallic compounds with as low as four carbon atoms in the amido carboxyl moiety, R, have been found to have satisfactory substantivity and hydrophobicity. It is preferable that the total number of carbon atoms in R not be too large, however, or substantivity is not satisfactory. It has been found that, in order for the organometallic compounds of the present invention to have suitable hydrophobicity and substantivity for a given application, the radicals $R^1$ and $R^2$ must be independently selected so that the sum of the carbon atoms in both $R^1$ and $R^2$ is not greater than 40, and is preferably within the range of 4 to 40, inclusive, and that the sum of the carbon atoms in the amido carboxyl moiety, R, must be at least 4.

The degree of substitution on the nitrogen atoms of the amido carboxyl moiety has also been observed to affect both the hydrophobicity and substantivity of the organometallic compound. In general, it has been found that tertiary amido carboxyl moieties are more hydrophobic than secondary amido carboxyl moieties, and at the same time are less substantive, especially to glass, than secondary amido carboxyl moieties. It will thus be appreciated that there is substantial flexibility in selecting either or both of $R^1$ and $R^2$ depending upon the requirements of the end use. For example, if hydrophobicity is of greatest importance and substantivity is of less significance, a tertiary amido carboxyl moiety may be employed as the R moiety. Conversely, if substantivity is of primary importance and hydrophobicity is less so, then a secondary amido carboxyl moiety may be employed as the R radical.

It should further be appreciated that the active moiety R' may, to some extent, also affect the properties of the compound. Specifically, the hydrophobicity of the compound may be affected. Any such effect which R' may have, should accordingly be taken into account in selecting $R^1$, $R^2$ and $R^3$.

It has been observed that the polarity of the active moiety, has an effect on the properties of the organometallic compound. Generally, as the polarity of the active moiety increases, the solubility of the compound in polar organic solvents increases. Increased solubility generally relates to improved film-forming and substantivity, but does not necessarily increase hydrophobicity.

Thus, in view of the substantial flexibility provided by the organometallic compounds of the present invention it will be appreciated that some experimentation may be required in order to define the chain length of R, and more particularly the desired chain length of each of the radicals $R^1$, $R^2$ and $R^3$ for selected active moieties R', in order to achieve the overall desired properties of the final compound.

Amido carboxyl moieties corresponding to formula (a) above which have been found suitable for preparing the organometallic compounds of the present invention include amido carboxyl moieties derived from maleamic acid, phthalamic acid and succinamic acid. For maleamic acid derived amido carboxyl moieties, $R^3$ in the above formula is an ethenylene radical, $CH=CH$. For phthalamic acid derived amido carboxyl moieties, $R^3$ in the above formula is a phenylene radical $C_6H_4$. And, for succinamic acid derived amido carboxyl moieties, $R^3$ in the above formula is an ethylene radical, $CH_2CH_2$. Preferred derivatives are dependent on R', the active moiety.

Illustrative of derivatives of succinamic acid which are suitable for use in the present invention are:
N-dodecylsuccinamate, N-octylsuccinamate,
N-hexylsuccinamate, N-octadecylsuccinamate,
N-tetradecylsuccinamate, N-hexadecylsuccinamate,
N-propylsuccinamate, N-isopropylsuccinamate
N,N-dioctadecylsuccinamate, N,N-dipropylsuccinamate,
N-4-dodecylphenylsuccinamate, N-propyl-2-dodecenylsuccinamate,
and N,N-dilaurylsuccinamate.

Preferred derivatives are dictated by specific end use applications. For example, by way of illustration and not limitation, a derivative of succinamic acid for an emollient application is N-tetradecylsuccinamate; a preferred derivative of succinamic acid for a sunscreen application is N-dodecylsuccinamate.

Illustrative of a suitable maleamic acid derivative is N-dodecylmaleamate. Illustrative of derivatives of phthalamic acid which have been found suitable are N-dodecylphthalamate and N-dodecyl-tetrabromophthalamate.

Amido carboxyl moieties corresponding to formula (b) above which have been found suitable for use in the organometallic compounds of the present invention include amido carboxyl moieties derived from sarcosine and proteins.

In sarcosine derived amido carboxyl moieties, $R^2$ is a methyl radical and $R^1$ is preferably a long chain fatty group. Exemplary of sarcosine derivatives which have been found suitable are cocoylsarcosine, oleoylsarcosine and lauroylsarcosine.

Preferred amido carboxyl moieties derived from naturally occurring proteins include acylated protein hydrolysates. Especially preferred is the acylated protein hydrolysate made from Maypon ®4C (a registered trademark of Inolex Chemical Company). Maypon®4C is identified by the Cosmetic, Toiletry and Fragrance Association as potassium cocoa hydrolyzed animal protein.

The active moiety, R', of the organometallic compounds of the present invention may be any moiety which enables the compound to perform a specific chemical, biological or physical function. In one aspect the active moiety may be derived from an organic compound which is itself known to be functionally efficacious for a selected end use, and which maintains its functional efficacy when bonded to the metal, such as, by way of example, an organic compound capable of absorbing ultraviolet radiation. In another aspect, the active moiety may be derived from an organic compound which is not necessarily functionally efficacious for the selected end use, but which, when bonded to the amido carboxyl moiety-metal environment of the organometallic compounds of this invention, becomes effective for that purpose.

With respect to these aspects, it is contemplated that the active moiety may itself be a film former, or it may assist in the film-forming characteristic of the organometallic compound. In particular, it is within the scope of the present invention that R', the active moiety, can be an amido carboxyl moiety, R, as set forth above. Organometallic compounds wherein both R and R' are amido carboxyl moieties have been found to have superior film-forming characteristics and substantivity. It is likewise contemplated that the amido carboxyl moiety may include atoms, such as, for example, halogen, or other radicals, which may impart activity. Illustrative of an halogen containing amido carboxyl moiety is N-dodecyltetrabromophthalamate. Illustrative of other amido carboxyl moieties which include an active group are N-tetradecylsuccinamate, N-hexadecylsuccinamate, N-dodecylsuccinamate, N-lauroylsarcosinate, N-cocoylsarcosinate, and N-oleylsarcosinate.

Any organic radical which is capable of bonding to the metal may be suitably employed as the active moiety. To promote facile bonding to the metal, the active moiety preferably contains an active (that is, acidic) hydrogen atom.

Typically, bonding of the active moiety R' to the metal may be accomplished by a suitable organic linkage which may be a part of the active moiety, such as, for example, a carboxylate, sulfonate, phosphate, phosphite, oxa, or thia linkage. It will be appreciated that bonding of the modifier moiety, R", to the metal may likewise be through such linkages.

Because of the wide variety of organic radicals which may be suitably employed as the active moiety, the organometallic compounds of the present invention may be tailored to a myriad of specific end use applications. Broadly stated, the active moiety may be selected so as to provide organometallic compounds suitable for use in such diverse fields and industries as cosmetics, industrial coatings, agriculture, textiles and leather, pharmaceuticals, photography, paint and ink, and plastics.

By appropriate selection of the active moiety, the organometallic compounds of the present invention may be satisfactorily employed, for example, in the following: in wood coatings, such as, for example, polishes, preservatives, waxes, waterproofing, ultraviolet absorber and the like; in metal coatings such as polishes, corrosion inhibitors, sealers, paints and the like, and in paper products as a fire retardant, as a water proofer and the like; in textile and leather, including use as wrinkle reducers, flame retardants, sizing, waterproofing, sealing, permanent press, softener, mold release, antistat and the like; in agriculture, including herbicides, insecticides, insect repellants, seed protectant and the like; in pharmaceutical uses, such as a liquid bandage or wound dressing, topical application of drugs, antiseptic spray, encapsulating agent and the like; in cosmetics, including hair coloration, hair spray, hair conditioning, makeup, antiperspirant, perfume fixture, sunscreens, emollients and the like; in photography, including use as a support, overcoat, antistat, ultraviolet radiation absorber, and the like; in paints and inks, such as, as an adhesive, an additive or the like; and in plastics, such as a photocuring additive or ultraviolet radiation absorber. Many other active moieties and end uses will be apparent to those skilled in the art.

Specific examples of active moieties and their intended application are discussed below. These examples are illustrative of, and not in limitation of, the active moieties that may find utility in the organometallic compounds of the present invention. For example, a suitable example of a herbicide active moiety is α-2,4-dichlorophenoxyacetate; an example of an insect repellent active moiety is monomethyl phthalate. Examples of ultra-violet absorbers used as active moieties include p-dimethylaminobenzoate, p-aminobenzoate, urocanate, p-methoxycinnamate, salicylate and 2-benzoyl-4-methoxyphenoxide.

Other types of active moieties include alkyl carboxylates having from about 6 to about 32 carbon atoms, unsaturated alkyl carboxylates, branched alkyl carboxylates and the like. The alkyl groups may be substituted or perhalogenated.

Examples of active moieties capable of imparting emolliency to the organometallic compounds of this invention include myristate, oleate, isostearate, 12-hydroxystearate, and carboxylates of dimer acids.

The organometallic compounds of the present invention further include at least one modifier moiety, R", in order to satisfy the valency of the metal M. The number of modifier moieties required will, of course, depend upon the valency of the metal. Where the metal is trivalent, only one such modifier moiety will be required. Where the metal is tetravalent, then two modifier moieties will be required. When two modifier moieties are required, they may be the same or different. For ease of synthesis, it is preferable for both modifier moieties to be the same. However, it will be appreciated that after synthesis, hydrolysis may occur, in whole or in part, so that the modifier moieties of the resulting compounds may be different. In general, mixtures of modifier moieties are anticipated.

The modifier moiety, R", may be an hydroxyl, an alkoxy radical of from 1 to about 6 carbon atoms, or a carboxyl radical of from 1 to about 6 carbon atoms. The specific size of the modifier moiety, R", is of primary concern because of steric hindrance. For example, it is known to the art that three stearate moieties will not bond to aluminum under the reaction conditions typically employed in the practice of the present invention. Accordingly, hydroxyl, or some other group, including alkoxy radicals of from 1 to about 3 carbon atoms, and carboxyl radicals of from 1 to about 3 carbon atoms are preferred.

The specific composition of the modifier moiety, R", has been found to appreciably affect the properties of the organometallic compounds of the present invention.

There is a direct relationship between the polar nature of an organic modifier moiety and the solubility of the organometallic compound in organic media, such as isopropyl alcohol, such that, as the polarity of R″ increases, the solubility of the organometallic compound likewise increases. However, when R″ is hydroxyl, the compounds are less soluble in alcohol and the film-forming characteristics, and substantivity of the organometallic compounds is generally diminished. It has also been observed that, generally, where the modifier moiety is a lower alkyl carboxylate radical, and, in particular acetate or lactate, the substantivity of the organometallic compound is improved. The effect of the modifier moiety on the properties of the organometallic compound of the present invention is illustrated in the examples. It has thus been observed that organometallic compounds, identical in all respects except for the modifier moiety, have different film-forming characteristics, substantivity and hydrophobicity. Where the metal is aluminum, titanium or zirconium, the modifier moiety R″ is preferably an hydroxyl, an isopropoxyl, an n-propoxyl, an acetate or a lactate radical. In the case of tin, the modifier moiety R″ is preferably a lower alkyl radical of from 1 to about 6 carbon atoms, preferably of from 1 to about 4 carbon atoms. The n-butyl radical is especially preferred.

With some organometallic compounds of the present invention, it has been observed that the desirable properties of the active moiety have been enhanced by their being bonded to the metal. Particularly, this has been observed in the preparation of emollients. For example, myristic acid is, itself, a poor emollient. However myristate, as the active moiety in the organometallic compounds described herein, resulted in a compound which has emollient properties which are superior to those of myristic acid.

Organometallic compounds of the present invention suitable for sunscreen applications, include N-dodecyl-succinamate-p-dimethylaminobenzoatealuminum isopropylate, N-oleoylsarcosinate-p-dimethylaminobenzoatezirconium bis-n-propylate, or N-octylsuccinamate-p-aminobenzoatedibutyltin.

Formulations into which the organometallic compounds of this invention may be incorporated, as for example, a cosmetic formulation or the like, exhibit desirable properties. As an illustration, improved efficacy may result because the active moiety is held to the substrate. In addition, product design flexibility is enhanced because of the wide variety of active moieties that may be used to make the organometallic compound.

In accordance with another aspect of the present invention, a composition comprising a mixture or mixtures of the organometallic compounds described in detail herein above is anticipated. The organometallic compositions of the present invention may thus include organometallic compounds in which R and R′ are the same or different, including, for example, organometallic compounds which comprise two or more active moieties, R′, bonded to the metal, and organometallic compositions which comprise two or more amido carboxyl moieties, R, bonded to the metal. More particularly, organometallic compositions are contemplated which have the formula

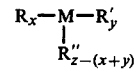

wherein M, R, R′ and R″ represent materials or mixtures of materials selected from the group comprising respectively, trivalent or tetravalent metals, amido carboxyl moieties, active moieties and modifier moieties, and are the same, respectively, as they are for the organometallic compounds described above. In this formula x and y are each greater than 0 and equal to or less than 2, the sum of x and y is less than z, and z is the valency of the metal.

The general formula of the organometallic compositions of the present invention set forth above is not intended to indicate the actual structure of any organometallic composition, but is, instead, intended to indicate the average stoichiometry between the metal M and the moieties R, R′ and R″. Preferred compositions are those wherein the stoichiometry is such that x is from 0.5 to 1.5 and y is from 0.5 to 1.5; and most preferably those in which x and y are each about one.

It will be appreciated to those skilled in the metallosoap art that there are many synthetic routes which may be utilized in order to make the organometallic compounds and compositions of the present invention.

As one example, synthesis of the organometallic compounds and compositions of the present invention comprises the reaction of an organometallic starting material with the appropriate active hydrogen containing compounds to effect substitution at the metal with, respectively, the amido carboxyl moieties, active moieties and modifier moieties of choice. For organometallic compositions of the present invention in which the metal is aluminum, zirconium or titanium, it is preferred to use a metalalkoxide starting material. Specifically, for the organoaluminum compounds, the preferred starting material is aluminum isopropoxide. For the organozirconium compounds, the preferred starting material is zirconium tetra-n-propoxide. For the organotitanium compounds, the preferred starting material is titanium tetraisopropoxide.

One reaction sequence which may be followed to provide the organometallic compounds and compositions of this invention can be described as follows:

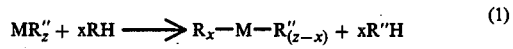

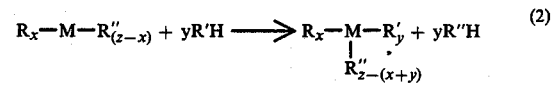

Optionally, the organometallic composition of step (2) may be further reacted, in whole or in part, to produce compositions where R″ is different from that in the starting material as, for example, as shown below in the case of water:

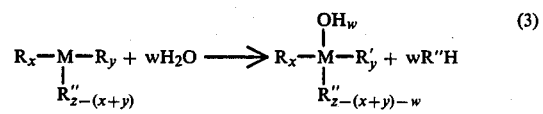

where w is greater than 0 and equal to or less than z-(x+y).

While there are other synthetic routes which should be apparent to those skilled in the art that may be used in preparing the compositions of this invention, the synthetic route described above is preferred because it allows for the greatest flexibility in the R, R' and R" moieties of the final product. By way of example, the stoichiometry of the reaction synthesis can be suitably selected to provide a composition in which R may be a single amido carboxyl moiety or a mixture of amido carboxyl moieties, and/or R' may be a single active moiety or a mixture of active moieties, and/or R" may be a single modifier moiety or a mixture of modifier moieties. Further, the modifier moiety of the final composition can be changed in whole or in part by subsequent reaction of the composition with a second modifier moiety as shown in equation (3). For example, if the starter is aluminum isopropoxide, R" in the final product will be isopropoxide in equation (2) (R" may also be hydroxide due to hydrolysis of the isopropoxide, equation (3)). The isopropoxyl containing composition may be reacted with a lower alkyl carboxylic acid, such as, for example, acetic acid, in order to substitute the isopropoxyl radical with a lower alkyl carboxylate (acetate).

For organotin compositions of the present invention, the preferred starting material is an alkyltin oxide, and the resulting composition has the general formula:

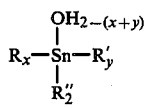

wherein R is the amido carboxyl moiety, R' is the active moiety, R" is an alkyl radical and x and y are each greater than 0 and less than 2, and the sum of x and y is greater than 1 and less than or equal to 2.

In a synthesis of organotin compositions in accordance with the present invention, a dialkyltin oxide, preferably dibutyltin oxide, is reacted sequentially with the active hydrogen containing organic compounds, for example, where x and y are each equal to one, by the following synthetic route:

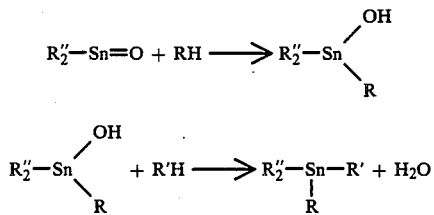

In preparing organotin compositions of the present invention, hydroxyl radicals may be substituted, in whole or in part, with an active moiety or modifier moiety, by a reaction with an active hydrogen containing organic compound. For example, reaction of the hydroxyl with a lower alkyl carboxylate may be readily accomplished.

DEFINITIONS

As used in the Examples appearing below, the following designations, symbols, terms and abbreviations have the indicated meanings:

Maypon ®4C denotes cocoa hydrolyzed animal protein, derived from the protein salt commercially available from Inolex Chemical Company, after reaction with the organometallic starting material;

Bio-Soft ®S-100 (a registered trademark of Stepan Company) denotes dodecylbenzenesulfonic acid, after reaction with the organometallic starting material;

DMPABA denotes p-dimethylaminobenzoic acid, after reaction with the organometallic starting material;

PABA denotes p-aminobenzoic acid, after reaction with the organometallic starting material;

Hamposyl ®C denotes cocoylsarcosine, commercially available from W.R. Grace & Co., after reaction with the organometallic starting material;

Hamposyl ®L denotes lauroylsarcosine, commercially available from W.R. Grace & Co., after reaction with the organometallic starting material;

Hamposyl ®O denotes oleoylsarcosine, commercially available from W.R. Grace & Co., after reaction with the organometallic starting material;

FF denotes film-forming property;

SUB denotes substantivity; and

HPB denotes hydrophobicity.

PROCEDURES

The following test procedures were employed to evaluate the organometallic compounds and compositions of the present invention.

SUBSTANTIVITY AND FILM-FORMING TEST

A substantivity and film-forming test was developed in order to characterize the organometallic compounds of this invention and to provide a standard for comparing them.

The following procedure was used in carrying out the film-forming test:

A 1"×3" glass microscope slide was dipped into a 7% isopropyl alcohol solution/slurry of the organometallic compound to be tested. These slides were allowed to dry for thirty minutes. If a thick film resulted, the compound was wiped to a thin film of less than 3 mils in thickness before it dried for the test.

Each material was then graded in three separate categories, namely film-forming property, hydrophobicity and substantivity. The criteria used in each category are set out below:

A. Film-Forming Property. The film-forming characteristic or property of the organometallic compounds were graded as follows:

+continuous uniform film o continuous nonuniform film

−not continuous, nonuniform; "spotty", powdery, or "chalky" in appearance.

B. Hydrophobicity. The hydrophobicity of the film was determined by running 55° C. tap water over the coated plates for sixty seconds. The material on the plates was then graded by visual observation as follows:

+75–100% of the material remains on the plate.

o 50–75% of the material remains on the plate.

−50% of the material remains on the plate.

C. Substantivity. The substantivity of the film was graded as follows:

+Material cannot be removed or can only be removed with very forceful rubbing.

o Material can be removed with rubbing, but displays some adhesive properties.

−Material is readily removed with rubbing.

A substantivity of "o" or "+" denotes that the resulting material is substantive as that term is defined herein.

The following examples are illustrative of and not in limitation of this invention.

EXAMPLE 1

This Example illustrates the preparation of N-dodecylsuccinamate-p-dimethylaminobenzoatealuminum isopropylate. The active moiety absorbs ultraviolet radiation, and the composition is thus suitable for use as a sunscreen.

Aluminum isopropoxide, (0.044 mole, 8.97 grams) was placed in a one liter, four-neck, round bottom flask fitted with a mechanical stirrer, an Allihn condenser, nitrogen sparge, and an addition funnel. Dry isopropyl alcohol, 143 ml, was added and the mixture stirred and refluxed for fifteen minutes. The addition funnel was charged with N-dodecylsuccinamic acid (0.044 mole, 12.54 grams) dissolved in 50 ml isopropyl alcohol. The N-dodecylsuccinamic acid solution was added slowly, over twenty minutes, to the refluxing aluminum isopropoxide solution. Refluxing was continued for one hour and p-dimethylaminobenzoic acid (0.044 mole, 7.26 grams) dissolved in 167 ml of hot isopropyl alcohol, was added all at once. After an additional two hour reflux, three-fourths of the reaction mixture was allowed to cool to room temperature; the remaining one-fourth was treated as described below. A fine, white suspension was obtained and characterized by IR and proton NMR analyses.

The fine white suspension so obtained was found to be substantive to skin, it did not wash off with water, and showed an enhancement in the UV spectrum.

This compound was graded as follows:
film-forming property: +
substantivity: o
hydrophobicity: +.

The remaining one-fourth of the reactive mixture produced above was reacted with water to convert a portion of the isopropylate to hydroxyl, as follows.

Before the reaction mixture was allowed to cool, 0.011 mole of water was added to the mixture all at once. The resulting mixture was then refluxed for an additional 15 minutes. It was found that about 70% of the N-dodecylsuccinamate-p-dimethylaminobenzoate aluminumisopropylate was converted to N-dodecylsuccinamate-p-dimethylaminobenzoate aluminum-hydroxide.

In like fashion, the modifier moiety, R'', can be converted to a carboxylate by appropriate reaction with a carboxylic acid.

EXAMPLE 2

This Example illustrates the preparation of Maypon ®4C myristatealuminum hydroxide, which is suitable for use as an emollient.

Octylisononanoate, 39.4 grams, and Maypon ®4C acids (41% solids in isopropyl alcohol, 68.9 grams), were placed in a 250 ml beaker fitted with a magnetic stirrer. The isopropyl alcohol was removed by heating the mixture to 105° C. Aluminum isopropylate cyclic trimer (12.3% aluminum content in isopropyl palmitate, 14.3 grams) was then added all at once. The reaction mixture was heated at 93° C for one hour. Myristic acid (14.7 grams) was added and the reaction allowed to stir at 93° C for one hour. The final product is a clear, viscous liquid.

EXAMPLES 3–130

Examples 3–130 illustrate various organoaluminum compounds of the present invention. These compounds were made in accordance with the procedure of Example 1. The compounds have the formula:

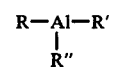

The specific amido carboxyl moiety, active moiety and modifier moiety of the compounds, as well as the film-forming characteristics, hydrophobicity and substantivity (according to the procedures set forth above) for these compounds, are set forth in Table I:

TABLE I

| Ex. No. | R | R' | R'' | FF | SUB | HPB |
|---|---|---|---|---|---|---|
| 3 | succinamate | PABA | hydroxyl | − | − | o |
| 4 | succinamate | PABA | acetate | − | o | o |
| 5 | N—propylsuccinamate | DMPABA | hydroxyl | + | + | − |
| 6 | N—propylsuccinamate | DMPABA | acetate | + | + | − |
| 7 | N—propylsuccinamate | PABA | hydroxyl | o | o | − |
| 8 | N—propylsuccinamate | benzoate | hydroxyl | + | + | − |
| 9 | N—propylsuccinamate | benzoate | acetate | + | + | − |
| 10 | N—propylsuccinamate | pyruvate | hydroxyl | + | + | o |
| 11 | N—propylsuccinamate | pyruvate | acetate | + | + | − |
| 12 | N—hexylsuccinamate | DMPABA | hydroxyl | o | + | − |
| 13 | N—hexylsuccinamate | DMPABA | acetate | + | + | − |
| 14 | N—hexylsuccinamate | PABA | hydroxyl | − | o | + |
| 15 | N—hexylsuccinamate | PABA | acetate | − | + | + |
| 16 | N—hexylsuccinamate | PABA | isopropoxyl | o | o | o |
| 17 | N—hexylsuccinamate | benzoate | hydroxyl | o | + | − |
| 18 | N—hexylsuccinamate | benzoate | acetate | + | + | o |
| 19 | N—hexylsuccinamate | pyruvate | hydroxyl | + | + | + |
| 20 | N—hexylsuccinamate | pyruvate | acetate | + | + | + |
| 21 | N—octylsuccinamate | DMPABA | hydroxyl | + | + | − |
| 22 | N—octylsuccinamate | DMPABA | acetate | + | + | + |
| 23 | N—octylsuccinamate | PABA | hydroxyl | o | o | + |
| 24 | N—octylsuccinamate | benzoate | hydroxyl | − | o | + |
| 25 | N—octylsuccinamate | benzoate | acetate | o | + | + |
| 26 | N—octylsuccinamate | pyruvate | hydroxyl | + | + | + |
| 27 | N—octylsuccinamate | pyruvate | acetate | + | + | + |
| 28 | N—dodecylsuccinamate | DMPABA | hydroxyl | + | o | + |
| 29 | N—dodecylsuccinamate | DMPABA | acetate | + | o | + |
| 30 | N—dodecylsuccinamate | DMPABA | lactate | o | + | o |
| 31 | N—dodecylsuccinamate | PABA | hydroxyl | − | o | + |

TABLE I-continued

| Ex. No. | R | R' | R" | FF | SUB | HPB |
|---|---|---|---|---|---|---|
| 32 | N—dodecylsuccinamate | PABA | acetate | + | + | + |
| 33 | N—dodecylsuccinamate | PABA | isopropoxyl | − | o | + |
| 34 | N—dodecylsuccinamate | benzoate | hydroxyl | + | o | + |
| 35 | N—dodecylsuccinamate | benzoate | acetate | + | + | + |
| 36 | N—tetradecylsuccinamate* | DMPABA | hydroxyl | − | − | + |
| 37 | N—tetradecylsuccinamate* | DMPABA | acetate | − | − | + |
| 38 | N—tetradecylsuccinamate | DMPABA | lactate | + | o | o |
| 39 | N—tetradecylsuccinamate* | PABA | hydroxyl | − | − | + |
| 40 | N—tetradecylsuccinamate* | PABA | acetate | − | − | o |
| 41 | N—tetradecylsuccinamate | PABA | lactate | + | + | o |
| 42 | N—tetradecylsuccinamate* | benzoate | hydroxyl | + | − | + |
| 43 | N—tetradecylsuccinamate | benzoate | acetate | o | o | + |
| 44 | N—tetradecylsuccinamate | benzoate | lactate | + | + | o |
| 45 | N—tetradecylsuccinamate | pyruvate | hydroxyl | + | o | + |
| 46 | N—tetradecylsuccinamate | pyruvate | acetate | o | + | + |
| 47 | N—tetradecylsuccinamate | pyruvate | lactate | o | + | − |
| 48 | N—hexadecylsuccinamate* | DMPABA | hydroxyl | − | − | + |
| 49 | N—hexadecylsuccinamate | DMPABA | acetate | − | − | + |
| 50 | N—hexadecylsuccinamate | DMPABA | lactate | + | + | + |
| 51 | N—hexadecylsuccinamate* | PABA | acetate | − | − | + |
| 52 | N—hexadecylsuccinamate | PABA | lactate | + | + | + |
| 53 | N—hexadecylsuccinamate* | benzoate | hydroxyl | − | − | + |
| 54 | N—hexadecylsuccinamate | benzoate | acetate | o | o | + |
| 55 | N—hexadecylsuccinamate | benzoate | lactate | − | o | − |
| 56 | N—hexadecylsuccinamate* | pyruvate | hydroxyl | − | − | + |
| 57 | N—hexadecylsuccinamate | pyruvate | acetate | + | + | + |
| 58 | N—hexadecylsuccinamate | pyruvate | lactate | − | + | − |
| 59 | N—octadecylsuccinamate | DMPABA | hydroxyl | − | − | + |
| 60 | N—octadecylsuccinamate | DMPABA | acetate | + | o | + |
| 61 | N—octadecylsuccinamate | PABA | hydroxyl | + | o | + |
| 62 | N—octadecylsuccinamate | benzoate | hydroxyl | o | − | + |
| 63 | N—octadecylsuccinamate | benzoate | acetate | + | o | + |
| 64 | Hamposyl ® C | PABA | hydroxyl | + | o | o |
| 65 | Hamposyl ® C | PABA | acetate | − | + | − |
| 66 | Hamposyl ® L | PABA | hydroxyl | + | o | + |
| 67 | Hamposyl ® L | PABA | acetate | + | + | + |
| 68 | Hamposyl ® O | PABA | hydroxyl | + | o | + |
| 69 | Hamposyl ® O | PABA | acetate | − | + | o |
| 70 | Maypon ® 4C | DMPABA | hydroxyl | + | o | + |
| 71 | Maypon ® 4C | PABA | hydroxyl | + | + | − |
| 72 | 6-acetamidohexanoate | PABA | hydroxyl | − | o | − |
| 73 | N—acetylglycine | DMPABA | hydroxyl | − | − | − |
| 74 | N—acetylglycine | DMPABA | acetate | o | + | − |
| 75 | N—propyl-2-dodecenylsuccinamate | DMPABA | acetate | + | + | + |
| 76 | N—propyl-2-dodecenylsuccinamate | DMPABA | hydroxyl | o | o | + |
| 77 | N,N—dipropylsuccinamate | DMPABA | hydroxyl | + | o | + |
| 78 | N,N—dipropylsuccinamate | DMPABA | acetate | + | o | − |
| 79 | N,N—dipropylsuccinamate | PABA | hydroxyl | o | + | + |
| 80 | N,N—dipropylsuccinamate | benzoate | hydroxyl | o | + | o |
| 81 | N,N—dipropylsuccinamate | benzoate | acetate | + | + | + |
| 82 | N,N—didodecylsuccinamate | DMPABA | hydroxyl | − | − | + |
| 83 | N,N—didodecylsuccinamate | DMPABA | acetate | o | o | + |
| 84 | N,N—didodecylsuccinamate | PABA | acetate | + | o | + |
| 85 | N,N—didodecylsuccinamate | benzoate | hydroxyl | − | − | + |
| 86 | N,N—didodecylsuccinamate | benzoate | acetate | − | o | + |
| 87 | N,N—dioctadecylsuccinamate | DMPABA | hydroxyl | − | − | − |
| 88 | N,N—dioctadecylsuccinamate | DMPABA | acetate | + | + | + |
| 89 | N,N—dioctadecylsuccinamate | PABA | hydroxyl | o | − | − |
| 90 | N,N—dioctadecylsuccinamate | benzoate | hydroxyl | − | − | + |
| 91 | N,N—dioctadecylsuccinamate | benzoate | acetate | + | + | + |
| 92 | N—dodecylsuccinamate | Bio Soft ® S-100 | hydroxyl | + | o | + |
| 93 | N—dodecylsuccinamate | Bio Soft ® S-100 | acetate | + | o | + |
| 94 | N—dodecylsuccinamate | bishexadecylphosphate | hydroxyl | + | o | + |
| 95 | N—dodecylsuccinamate | diethylphosphate | hydroxyl | o | − | + |
| 96 | N—dodecylsuccinamate | diethylphosphate | acetate | + | + | + |
| 97 | N—dodecylsuccinamate | dodecanthiol | hydroxyl | − | − | + |
| 98 | N—dodecylsuccinamate | octoxide | hydroxyl | + | + | + |
| 99 | N—dodecylsuccinamate | octoxide | acetate | + | + | + |
| 100 | Maypon ® 4C | methylsulfate | hydroxyl | + | + | + |
| 101 | N—octylsuccinamate | acetylsalicylate | acetate | + | + | + |
| 102 | N—octylsuccinamate | acetylsalicylate | isopropoxyl | + | + | + |
| 103 | N—dodecylsuccinamate | 2,2'-dihydroxy-4,4'-dimethoxybenzophenone | hydroxyl | o | + | + |
| 104 | N—dodecylsuccinamate | 2,2'-dihydroxy-4,4'-dimethoxybenzophenone | acetate | o | + | + |

TABLE I-continued

| Ex. No. | R | R' | R" | FF | SUB | HPB |
|---|---|---|---|---|---|---|
| 105 | N—dodecylsuccinamate | 2,4-dichlorophenoxyacetate | hydroxyl | + | + | + |
| 106 | N—dodecylsuccinamate | 2,4-dichlorophenoxyacetate | acetate | + | + | + |
| 107 | N—dodecylsuccinamate | acetylsalicylate | hydroxyl | + | + | + |
| 108 | N—dodecylsuccinamate | acetylsalicylate | acetate | + | + | + |
| 109 | N—dodecylsuccinamate | ascorbate | hydroxyl | + | + | — |
| 110 | N—dodecylsuccinamate | ascorbate | acetate | + | + | — |
| 111 | N—dodecylsuccinamate | ascorbate | isopropoxyl | + | + | — |
| 112 | Maypon ® 4C | 2-acetoylbenzoate | hydroxyl | + | + | — |
| 113 | Maypon ® 4C | 4-methoxycinnamate | hydroxyl | + | + | — |
| 114 | Maypon ® 4C | laurate | hydroxyl | + | o | + |
| 115 | Maypon ® 4C | uraconate | hydroxyl | + | + | — |
| 116 | Maypon ® 4C | monomethylphthalate | isoproxyl | + | + | — |
| 117 | Hamposyl ® L | myristate | hydroxyl | + | + | + |
| 118 | N—dodecylphthalate | DMPABA | hydroxyl | + | o | + |
| 119 | N—dodecylphthalate | DMPABA | hydroxyl | + | — | — |
| 120 | N—octylsuccinamate | lactate | lactate | + | o | + |
| 121 | N—octylsuccinamate | N—octylsuccinamate | hydroxyl | + | + | + |
| 122 | N—octylsuccinamate | N—octylsuccinamate | acetate | + | + | + |
| 123 | N—dodecylsuccinamate | N—dodecylsuccinamate | hydroxyl | + | + | + |
| 124 | N—dodecylsuccinamate | N—dodecylsuccinamate | acetate | + | + | + |
| 125 | N—tetradecylsuccinamate | N—tetradecylsuccinamate | hydroxyl | + | o | + |
| 126 | N—tetradecylsuccinamate | N—tetradecylsuccinamate | acetate | + | o | + |
| 127 | Hamposyl ® C | Hamposyl ® C | hydroxyl | + | + | + |
| 128 | N—dodecyltetrabromophthalamate | N—dodecyltetrabromophthalamate | isopropoxyl | o | + | + |
| 129 | N—tetradecylsuccinamate | N—tetradecylsuccinamate | lactate | + | o | + |
| 130 | Maypon ® 4C | Maypon ® 4C | hydroxyl | + | + | + |

*In these Examples, the hydroxyl content of the aluminum isopropylate was very high, and it is believed that the high hydroxyl content had an adverse effect on substantivity, as illustrated. However, it is further believed that with an aluminum isopropylate starting material with lower hydroxyl content that compounds having the desired substantivity would result.

The data in Table I demonstrates the effect that each of the amido carboxyl moiety, active moiety and modifier moiety may have on the properties of the organometallic compounds and compositions of the present invention and illustrates that the interdependency of these moieties must be taken into account in order to provide a compound or composition which not only has the desired activity for the contemplated end use, but which will also have the film-forming characteristic, substantivity and hydrophobicity to make the compound effective for that application.

For example, Examples 1–63 illustrate the effect of chain length of the amido carboxyl moiety on the film-forming property, substantivity and hydrophobicity of the organometallic compounds. In general, as the carbon chain length increases, substantivity decreases, although it is still satisfactory in most cases, while hydrophobicity increases. However, the modifier moiety can have significant effect on both substantivity and hydrophobicity, as illustrated in, for example, Examples 3 and 4, 14–16 and 28–30. Similarly, the effect of the polarity of the active moiety can also be seen from Examples 1–63. Generally, the greater the polarity of the active moiety, the greater the substantivity of the organometallic compounds and compositions. Further, Examples 5–91 illustrate the effect of a secondary versus tertiary amido carboxyl moiety. It can be seen that generally tertiary amido carboxyl moieties are more hydrophobic, but less substantive than secondary amido carboxyl moieties.

These Examples in general, and Examples 92–106 in particular, illustrate the wide variety of linkages on the active moiety through which bonding of the active moiety to the metal may be accomplished. Exemplary of the wide variety of active moieties that may be incorporated in the organometallic compounds of this invention are the compounds shown in Examples 101–120. Examples 121–130 illustrate organometallic compounds wherein the active moiety is itself a filmformer. As can be seen, these compounds exhibit superior film-forming characteristics.

Examples 118–119 illustrate the effect of the presence of water during the synthesis of the compounds of this invention. The product of Example 119 was made in the presence of excess water and the effect on substantivity and hydrophobicity can be seen when compared with Example 118.

EXAMPLE 131

This Example illustrates the preparation of Maypon®4C p-aminobenzoatetitanium diisopropoxide, which is useful as a sunscreen.

Titanium tetraisopropoxide (0.044 mole, 12.5 grams) in 143 ml of isopropyl alcohol was refluxed for fifteen minutes in a one liter, four-neck, round bottom flask fitted with a mechanical stirrer, an Allihn condenser, an addition funnel, and a nitrogen sparge. Maypon 4C acids (42.00 grams; 45.4% solids in IPA; 443 grams/mole, 0.044 mole) was added over a fifteen minute period to the refluxing solution. After one hour reflux, p-aminobenzoic acid (0.044 mole, 6.04 grams) in 169 ml of isopropyl alcohol was added all at once. The reaction mixture was refluxed for an additional two hours and cooled to room temperature. The bright orange solution gave an IR typical of a metal soap.

This compound was graded as follows:
film-forming property: +
substantivity: + hydrophobicity: o.

EXAMPLE 132

This Example illustrates the preparation of octylsuccinamate-p-aminobenzoatedibutyltin. The active moiety is an ultraviolet absorber and the composition is useful as a sunscreen.

Dibutyltin oxide (0.25 mole, 62.2 grams) in 300 ml dry benzene was placed in a 500 ml round bottom flask fitted with a magnetic stirrer, a Dean-Stark trap, and a nitrogen sparge. Octylsuccinamic acid (0.25 mole, 57.3 grams) in 100 ml benzene, was added slowly to the refluxing mixture and the hazy suspension became clear. p-Aminobenzoic acid (0.25 mole, 34.3 grams) was added all at once and the reaction mixture refluxed for four hours. The benzene was removed in vacuum and the oil product characterized by IR and proton NMR. This compound was graded as follows:
film-forming: +
substantivity: +
hydrophobicity: +.

EXAMPLE 133

This Example illustrates the preparation of oleoylsarcosinate-p-dimethylaminobenzoatezirconium bisn-propylate, which is useful as a sunscreen.

In a reaction vessel similar to that used in Example 1, zirconium tetrapropoxide (0.044 mole, 14.41 grams) in 143 ml of isopropyl alcohol was refluxed for fifteen minutes. Through the addition funnel, oleoylsarcosine (0.044 mole, 15.40 grams) in 50 ml of isopropyl alcohol was added over a fifteen minute period. After the mixture was refluxed for one hour, p-dimethylaminobenzoic acid (0.044 mole, 7.27 grams) in 163 ml of isopropyl alcohol was added all at once. The reaction mixture was refluxed an additional two hours and cooled to room temperature. The product was characterized by IR, UV, proton NMR analyses.

This compound was graded as follows:
film-forming: +
substantivity: o
hydrophobicity: +.

EXAMPLES 134–168

These Examples illustrate the preparation of organozirconium compounds with a wide variety of active and modifier moieties. These compounds were prepared in accordance with the procedure of Example 133.

The compounds have the general formula:

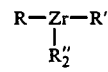

The specific amido carboxyl moiety, active moiety and modifier moiety of the compounds, as well as the film-forming characteristic, hydrophobicity and substantivity (according to the procedures set forth above) for these compounds are set forth in Table II.

TABLE II

| Ex. No. | R | R' | R'' | FF | SUB | HPB |
|---|---|---|---|---|---|---|
| 134 | N—propylsuccinamate | DMPABA | hydroxyl | — | o | + |
| 135 | N—propylsuccinamate | DMPABA | acetate | — | o | + |
| 136 | N—propylsuccinamate | DMPABA | propoxyl | — | o | — |
| 137 | N—isopropylsuccinamate | DMPABA | hydroxyl | + | o | + |
| 138 | N—isopropylsuccinamate | DMPABA | acetate | o | o | + |
| 139 | N—hexylsuccinamate | DMPABA | hydroxyl | + | o | + |
| 140 | N—hexylsuccinamate | DMPABA | acetate | + | o | + |
| 141 | N—hexylsuccinamate | DMPABA | propoxyl | + | o | + |
| 142 | N—octylsuccinamate | DMPABA | hydroxyl | + | + | + |
| 143 | N—octylsuccinamate | DMPABA | acetate | + | + | + |
| 144 | N—octylsuccinamate | DMPABA | propoxyl | + | + | + |
| 145 | N—dodecylsuccinamate | DMPABA | hydroxyl | + | o | + |
| 146 | N—dodecylsuccinamate | DMPABA | acetate | + | o | + |
| 147 | N—dodecylsuccinamate | DMPABA | lactate | + | + | + |
| 148 | N—dodecylsuccinamate | DMPABA | propoxyl | + | o | + |
| 149 | N—dodecylsuccinamate | salicylate | propoxyl | + | o | + |
| 150 | N—octadecylsuccinamate | DMPABA | hydroxyl | — | — | o |
| 151 | N—octadecylsuccinamate | DMPABA | acetate | — | — | + |
| 152 | N—octadecylsuccinamate | DMPABA | propoxyl | — | — | o |
| 153 | Hamposyl ® C | DMPABA | hydroxyl | + | o | + |
| 154 | Hamposyl ® C | DMPABA | acetate | + | o | + |
| 155 | Hamposyl ® C | DMPABA | lactate | o | o | + |
| 156 | Hamposyl ® C | DMPABA | propoxyl | o | o | + |
| 157 | Hamposyl ® L | DMPABA | acetate | + | o | + |
| 158 | Hamposyl ® L | DMPABA | lactate | + | o | + |
| 159 | Hamposyl ® L | DMPABA | propoxyl | + | o | + |
| 160 | Hamposyl ® O | DMPABA | acetate | + | o | + |
| 161 | Hamposyl ® O | DMPABA | lactate | + | o | + |
| 162 | Hamposyl ® O | DMPABA | propoxyl | + | o | + |
| 163 | Maypon ® 4C | 2-acetylbenzoate | propoxyl | + | o | + |
| 164 | Maypon ® 4C | Maypon ® 4C | propoxyl | + | + | + |
| 165 | Maypon ® 4C | PABA | propoxyl | + | o | + |
| 166 | N—dodecyltetrabromophthalamate | N—dodecyltetrabromophthalamate | propoxyl | o | o | o |

The effect of chain length of the amido carboxyl moiety and modifier moiety on film-forming, substantivity and hydrophobicity can be seen from these Examples. The wide variety of active moieties that can be included in organozirconium compounds of the present invention is also illustrated.

EXAMPLE 167

This Example illustrates the preparation of the organometallic composition (N-tetradecylsuccinamate)$_{1.25}$ (myristate)$_{1.25}$ aluminum(hydroxide)$_{0.5}$.

The composition was prepared by adding 45 grams of a 20% N-tetradecylsuccinamic acid solution in mineral oil to 29.5 grams of mineral oil in an open beaker, and heating the mixture to 93° C. Then, 4.7 grams of aluminum isopopylate was added and the mixture was held at 93° C. and stirred for 40 minutes. Myristic acid, 6.5 grams, was then added and the reaction mixture was stirred an additional 40 minutes at 93° C. Water, 0.2 grams, was then added to the warm reaction mixture and the mixture was allowed to cool to room temperature.

The organometallic composition so prepared may be used as an emollient.

Thus it can be seen that the present invention provides organometallic compounds and compositions which can be adapted for use in many and various applications. The organometallic compounds and compositions of this invention are substantive with respect to many types of substrates and desirably form films when applied to a substrate. The latitude permitted by the incorporation of an active moiety of choice allows the compound to be tailored to specific applications. Additionally the hydrophobicity of these compounds may be suitably controlled as desired.

We claim:

1. An organoaluminum compound having the general formula:

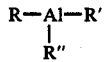

wherein R represents an amido carboxyl moiety selected from the group consising of:

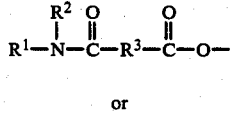

or

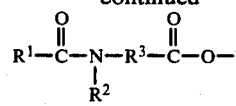

wherein $R^1$ and $R^2$ may be the same or different and are selected from the group consisting of hydrogen, an alkyl radical of from 1 to about 20 carbon atoms, an aryl or aralkyl radical of from 6 to about 20 carbon atoms, and an alkenyl radical of from 3 to about 20 carbon atoms; $R^3$ is a hydrocarbyl radical of from 1 to about 6 carbon atoms; and the sum of the carbon atoms in $R^1$ and $R^2$ is in the range of from 0 to about 40, and the sum of the carbon atoms in $R^1$, $R^2$ and $R^3$ is at least 2;

R″ is a modifier moiety selected from the group consisting of hydroxyl, an alkoxy radical of from 1 to about 6 carbon atoms, or a carboxyl radical of from 1 to about 6 carbon atoms;

R′, which may not be R or R″, comprises an active moiety, said active moiety being bonded to the aluminum by a linkage selected from the group consisting of carboxylate, sulfonate, phosphate, phosphite, oxa and thia linkages;

said organoaluminum compound forming a substantive coating when applied to a surface.

2. An organoaluminum compound according to claim 73 wherein R is selected from the group consisting of succinamate, N-akylsuccinamate wherein the alkyl has from 3 to about 18 carbon atoms, N,N dialkylsuccinamate wherein the alkyl has from 3 to about 18 carbon atoms, 6-acetamidohexanoate, N-acetylglycinate, N-alkylsarcosinate wherein the alkyl has from 1 to about 18 carbon atoms, coco hydrolysed animal protein and N-dodecyltetrabromophthalamate;

R′ is selected from the group consisting of p-dimethylaminobenzoate, p-aminobenzoate, salicylate, 2-acetylbenzoate, benzoate, diethylphosphate, dodecanthiol, bishexadecylphosphate, pyruvate, octoxide, methylsulfate, acetylsalicylate, 2,2′-dihydroxyl-4,4″-dimethoxybenzophenone, 2,4-dichlorophenoxyacetate, ascorbate, 4-methoxycinnamate, laurate, uraconate, monomethylphthalate, and myristate, and R″ is selected from the group consisting of hydroxyl, acetate, lactate, n-propoxyl and isopropoxyl.

* * * * *